United States Patent
Renner et al.

(10) Patent No.: US 7,211,272 B2
(45) Date of Patent: May 1, 2007

(54) DRUG DELIVERY DEVICE

(75) Inventors: Steven B. Renner, Rochester, NY (US); Matthew Jonasse, Sodus, NY (US)

(73) Assignee: Bausch & Lomb Incorporated, Rochester, NY (US)

(*) Notice: Subject to any disclaimer, the term of this patent is extended or adjusted under 35 U.S.C. 154(b) by 238 days.

(21) Appl. No.: 11/006,915

(22) Filed: Dec. 8, 2004

(65) Prior Publication Data

US 2005/0137583 A1 Jun. 23, 2005

Related U.S. Application Data

(60) Provisional application No. 60/532,022, filed on Dec. 22, 2003.

(51) Int. Cl.
*A61F 2/00* (2006.01)
*B29C 45/14* (2006.01)

(52) U.S. Cl. .................. 424/427; 264/516; 264/215

(58) Field of Classification Search ............... 424/422, 424/423, 427, 429; 264/27, 510, 512, 516, 264/212, 215, 216
See application file for complete search history.

(56) References Cited

U.S. PATENT DOCUMENTS

| | | | | |
|---|---|---|---|---|
| 3,961,628 A | * | 6/1976 | Arnold | 424/427 |
| 4,341,728 A | * | 7/1982 | Robertson et al. | 264/161 |
| 4,393,871 A | * | 7/1983 | Vorhauer et al. | 128/833 |
| 4,957,494 A | * | 9/1990 | Wong et al. | 604/892.1 |
| 5,378,475 A | | 1/1995 | Smith et al. | |
| 5,443,505 A | * | 8/1995 | Wong et al. | 623/4.1 |
| 5,589,176 A | * | 12/1996 | Seare, Jr. | 424/400 |
| 5,773,019 A | | 6/1998 | Ashton et al. | |
| 5,788,977 A | * | 8/1998 | Aguadisch et al. | 424/422 |
| 5,902,598 A | | 5/1999 | Chen et al. | |
| 6,001,386 A | | 12/1999 | Ashton et al. | |
| 6,217,895 B1 | | 4/2001 | Guo et al. | |
| 6,375,972 B1 | | 4/2002 | Guo et al. | |
| 6,713,081 B2 | * | 3/2004 | Robinson et al. | 424/427 |
| 6,773,713 B2 | * | 8/2004 | Bonassar et al. | 424/423 |
| 2002/0086051 A1 | | 7/2002 | Viscasillas | |
| 2002/0106395 A1 | | 8/2002 | Brubaker | |
| 2002/0110591 A1 | | 8/2002 | Brubaker et al. | |
| 2002/0110592 A1 | | 8/2002 | Brubaker et al. | |
| 2002/0110635 A1 | | 8/2002 | Brubaker et al. | |
| 2004/0265356 A1 | | 12/2004 | Mosack | |

OTHER PUBLICATIONS

Mosack et al., "Drug Delivery Device," U.S. Appl. No. 10/403,421, (Mar. 28, 2003).

* cited by examiner

*Primary Examiner*—Sharon E. Kennedy
(74) *Attorney, Agent, or Firm*—Glenn D. Smith; John E. Thomas

(57) ABSTRACT

A drug delivery device for placement in the eye includes a drug core comprising a pharmaceutically active agent, and a holder that holds the drug core. The holder is made of a material impermeable to passage of the active agent and includes an opening for passage of the pharmaceutically agent therethrough to eye tissue. The device includes a layer of material permeable to passage of the active agent. In assembling the device, a pin or weight, having a shape similar to the drug core, is used during curing of the permeable material.

20 Claims, 1 Drawing Sheet

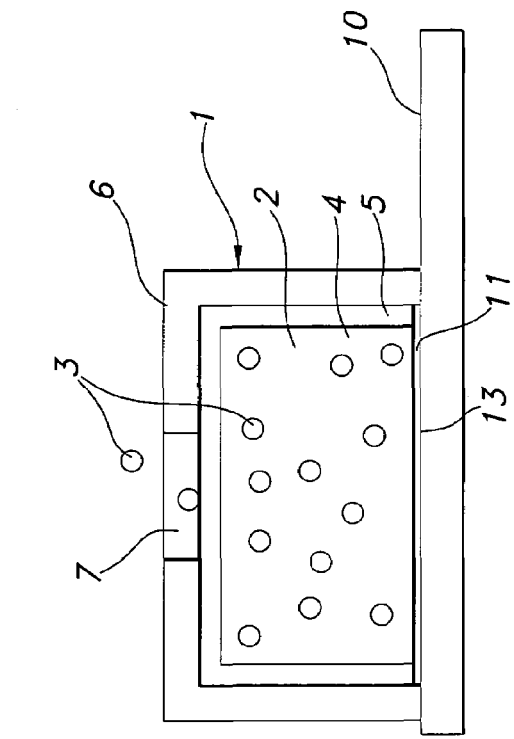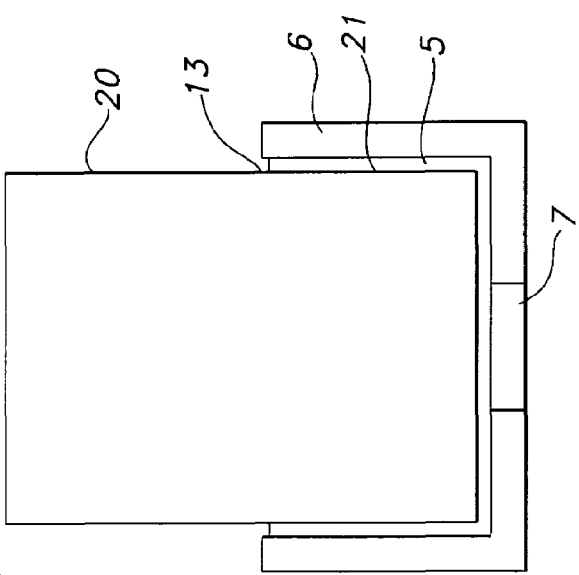

DRUG DELIVERY DEVICE

FIELD OF THE INVENTION

This invention relates to a drug delivery device, preferably a device that is placed or implanted in the eye to release a pharmaceutically active agent to the eye. The device includes a drug core and a holder for the drug core, wherein the holder is made of a material impermeable to passage of the active agent and includes at least one opening for passage of the pharmaceutically agent therethrough to eye tissue. Particularly, this invention provides improved methods of making such devices.

BACKGROUND OF THE INVENTION

Various drugs have been developed to assist in the treatment of a wide variety of ailments and diseases. However, in many instances, such drugs cannot be effectively administered orally or intravenously without the risk of detrimental side effects. Additionally, it is often desired to administer a drug locally, i.e., to the area of the body requiring treatment. Further, it may be desired to administer a drug locally in a sustained release manner, so that relatively small doses of the drug are exposed to the area of the body requiring treatment over an extended period of time.

Accordingly, various sustained release drug delivery devices have been proposed for placing in the eye and treating various eye diseases. Examples are found in the following patents, the disclosures of which are incorporated herein by reference: U.S. 2002/0086051A1 (Viscasillas); U.S. 2002/0106395A1 (Brubaker); U.S. 2002/0110591A1 (Brubaker et al.); U.S. 2002/0110592A1 (Brubaker et al.); U.S. 2002/0110635A1 (Brubaker et al.); U.S. Pat. No. 5,378,475 (Smith et al.); U.S. Pat. No. 5,773,019 (Ashton et al.); U.S. Pat. No. 5,902,598 (Chen et al.); U.S. Pat. No. 6,001,386 (Ashton et al.); U.S. Pat. No. 6,217,895 (Guo et al.); U.S. Pat. No. 6,375,972 (Guo et al.); U.S. patent application Ser. No. 10/403,421 (Drug Delivery Device, filed Mar. 28, 2003) (Mosack et al.); and U.S. patent application Ser. No. 10/610,063 (Drug Delivery Device, filed Jun. 30, 2003) (Mosack).

Many of these devices include an inner drug core including a pharmaceutically active agent, and some type of holder for the drug core made of an impermeable material such as silicone or other hydrophobic materials. The holder includes one or more openings for passage of the pharmaceutically agent through the impermeable material to eye tissue. Many of these devices include at least one layer of material permeable to the active agent, such as polyvinyl alcohol.

Various prior methods of making these types of devices involve the step of heat curing one of the materials from which the device is fabricated, such as the layer of permeable material, after insertion of the drug core in the device. This invention recognized that some active agents are heat sensitive, however, and such a heat curing step could deleteriously affect the active agent. This invention provides improved methods that avoid exposing the active agent in the drug core to excessive heat.

BRIEF DESCRIPTION OF THE DRAWINGS

FIG. 1 is a perspective view of a first embodiment of a drug delivery device of this invention.

FIG. 2 is a cross-sectional view of the device of FIG. 1.

FIG. 3 is a cross-sectional view of the device of FIGS. 1 and 2 during assembly.

FIG. 4 is a cross-sectional view of a second embodiment of a drug delivery device.

DETAILED DESCRIPTION OF PREFERRED EMBODIMENTS

FIGS. 1 and 2 illustrate a first embodiment of a device of this invention. Device 1 is a sustained release drug delivery device for implanting in the eye. Device 1 includes inner drug core 2 including a pharmaceutically active agent 3.

This active agent may include any compound, composition of matter, or mixture thereof that can be delivered from the device to produce a beneficial and useful result to the eye, especially an agent effective in obtaining a desired local or systemic physiological or pharmacological effect. Examples of such agents include: anesthetics and pain killing agents such as lidocaine and related compounds and benzodiazepam and related compounds; anti-cancer agents such as 5-fluorouracil, adriamycin and related compounds; anti-fungal agents such as fluconazole and related compounds; anti-viral agents such as trisodium phosphomonoformate, trifluorothymidine, acyclovir, ganciclovir, DDI and AZT; cell transport/mobility impending agents such as colchicine, vincristine, cytochalasin B and related compounds; antiglaucoma drugs such as beta-blockers: timolol, betaxolol, atenalol, etc; antihypertensives; decongestants such as phenylephrine, naphazoline, and tetrahydrazoline; immunological response modifiers such as muramyl dipeptide and related compounds; peptides and proteins such as cyclosporin, insulin, growth hormones, insulin related growth factor, heat shock proteins and related compounds; steroidal compounds such as dexamethasone, prednisolone and related compounds; low solubility steroids such as fluocinolone acetonide and related compounds; carbonic anhydrase inhibitors; diagnostic agents; antiapoptosis agents; gene therapy agents; sequestering agents; reductants such as glutathione; antipermeability agents; antisense compounds; antiproliferative agents; antibody conjugates; antidepressants; bloodflow enhancers; antiasthmatic drugs; antiparasiticagents; non-steroidal anti inflammatory agents such as ibuprofen; nutrients and vitamins: enzyme inhibitors: antioxidants; anticataract drugs; aldose reductase inhibitors; cytoprotectants; cytokines, cytokine inhibitors, and cytokin protectants; uv blockers; mast cell stabilizers; and anti neovascular agents such as antiangiogenic agents like matrix metalloprotease inhibitors.

Examples of such agents also include: neuroprotectants such as nimodipine and related compounds; antibiotics such as tetracycline, chlortetracycline, bacitracin, neomycin, polymyxin, gramicidin, oxytetracycline, chloramphenicol, gentamycin, and erythromycin; antiinfectives; antibacterials such as sulfonamides, sulfacetamide, sulfamethizole, sulfisoxazole; nitrofurazone, and sodium propionate; antiallergenics such as antazoline, methapyriline, chlorpheniramine, pyrilamine and prophenpyridamine; anti-inflammatories such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone and triminolone; miotics and anti-cholinesterase such as pilocarpine, eserine salicylate, carbachol, di-isopropyl fluorophosphate, phospholine iodine, and demecarium bromide; mydriatics such as atropine sulfate, cyclopentolate, homatropine, scopolamine, tropicamide, eucatropine, and hydroxyamphetamine; svmpathomimetics such as epinephrine; and prodrugs such as those described in Design of Prodrugs, edited by Hans Bundgaard, Elsevier Scientific Publishing Co., Amsterdam, 1985. In addition to the above agents, other agents suitable for treating, managing, or diagnosing conditions in a mammalian organism may be placed in the inner core and administered using the sustained release drug delivery devices of the current invention. Once again, reference may be made to any standard pharmaceutical textbook such as Remington's Pharmaceutical Sciences for the identity of other agents.

Any pharmaceutically acceptable form of such a compound may be employed in the practice of the present invention, i.e., the free base or a pharmaceutically acceptable salt or ester thereof. Pharmaceutically acceptable salts, for instance, include sulfate, lactate, acetate, stearate, hydrochloride, tartrate, maleate and the like.

As shown in the illustrated embodiment, active agent 3 may be mixed with a matrix material 4. Preferably, matrix material 4 is a polymeric material that is compatible with body fluids and the eye. Additionally, matrix material should be permeable to passage of the active agent 3 therethrough, particularly when the device is exposed to body fluids. For the illustrated embodiment, the matrix material is PVA. Also, in this embodiment, inner drug core 2 may be coated with a coating 5 of additional matrix material which may be the same or different from material 4 mixed with the active agent. For the illustrated embodiment, the coating 5 employed is also PVA.

Device 1 includes a holder 6 for the inner drug core 2. Holder 6 is made of a material that is impermeable to passage of the active agent 3 therethrough. Since holder 6 is made of the impermeable material, at least one passageway 7 is formed in holder 6 to permit active agent 3 to pass therethrough and contact eye tissue. In other words, active agent passes through any permeable matrix material 4 and permeable coating 5, and exits the device through passageway 7. For the illustrated embodiment, the holder is made of silicone, especially polydimethylsiloxane (PDMS) material.

A prior method of making a device of the type shown in FIGS. 1 and 2 includes the following procedures. A cylindrical cup of silicone is separately formed, for example by molding, having a size generally corresponding to the drug core tablet and a shape as generally shown in FIG. 2. This silicone holder is then extracted with a solvent such as isopropanol. Openings 7 are placed in silicone, for example, by boring or with the laser. A drop of liquid PVA is placed into the holder through the open end 13 of the holder, this open end best seen in FIG. 3. Then, the inner drug core tablet is placed into the silicone holder through the same open end 13 and pressed into the cylindrical holder. As a result, the pressing of the tablet causes the liquid PVA to fill the space between the tablet inner core and the silicone holder, thus forming permeable layer 5 shown in FIGS. 1 and 2. For the illustrated embodiment, a layer of adhesive 11 is applied to the open end 13 of the holder to fully enclose the inner drug core tablet at this end. Tab 10 is inserted at this end of the device. The liquid PVA and adhesive are cured by heating the assembly.

As mentioned, this invention recognized that some active agents are heat sensitive, the exposure of the inner drug core to heat curing could deleteriously affect the active agent. This invention provides improved methods that avoid exposing the active agent in the drug core to excessive heat.

According to a first embodiment of this invention, a curable liquid is placed in holder 6, and then, pin 20 is inserted in the holder 6 to displace this liquid, as illustrated in FIG. 3. Pin 20 may be made of a metal such as stainless steel or other non-corrosive materials. Then, the liquid is cured, such as by heat curing, and pin 20 is removed. Accordingly, the cured liquid forms coating 5. Pin 20 is removed, and inner drug core 2 may now be inserted in the holder 6 through end 13, in place of pin 20. It will be appreciated that lower end 21 of pin 20 preferably has a size and shape generally corresponding to the size and shape of inner drug core 2.

As in the aforementioned method, a layer of adhesive 11 may now be applied to the open end 13 of the holder to fully enclose the inner drug core tablet at this end. Tab 10 is inserted at this end of the device against the adhesive, so the device assumes the appearance as in FIG. 2.

For the illustrated embodiment, the active agent may be provided in the form of a micronized powder, and then mixed with an aqueous solution of the matrix material, in this case PVA, whereby the active agent and PVA agglomerate into larger sized particles. The resulting mixture is then dried to remove some of the moisture, and then milled and sieved to reduce the particle size so that the mixture is more flowable. Optionally, a small amount of inert lubricant, for example, magnesium stearate, may be added to assist in tablet making. This mixture is then formed into a tablet using standard tablet making apparatus, this tablet representing inner drug core 2.

An alternate embodiment is illustrated in FIG. 4. In this embodiment, the device further includes a disc 14 made of permeable material covering passageway 7 between the holder 6 and layer 5. For the illustrated embodiment, disc 14 may be preformed from PVA, similar to the material used for layer 5 and matrix material 4. In assembling this embodiment, disc 14 is placed in holder 6 prior to adding the liquid curable material forming layer 5. Then, pin 20 is used to displace the liquid, as in the previous embodiment. A potential advantage of this embodiment is that the thickness of the permeable materials at passageway 7 can be controlled better, thereby providing more consistent release of active through the permeable materials into passageway 7.

In addition to the illustrated materials, a wide variety of materials may be used to construct the devices of the present invention. The only requirements are that they are inert, non-immunogenic and of the desired permeability. Materials that may be suitable for fabricating the device include naturally occurring or synthetic materials that are biologically compatible with body fluids and body tissues, and essentially insoluble in the body fluids with which the material will come in contact. The use of rapidly dissolving materials or materials highly soluble in body fluids are to be avoided since dissolution of the wall would affect the constancy of the drug release, as well as the capability of the device to remain in place for a prolonged period of time.

Naturally occurring or synthetic materials that are biologically compatible with body fluids and eye tissues and essentially insoluble in body fluids which the material will come in contact include, but are not limited to, glass, metal, ceramics, polyvinyl acetate, cross-linked polyvinyl alcohol, cross-linked polyvinyl butyrate, ethylene ethylacrylate copolymer, polyethyl hexylacrylate, polyvinyl chloride, polyvinyl acetals, plasticized ethylene vinylacetate copolymer, polyvinyl alcohol, polyvinyl acetate, ethylene vinylchloride copolymer, polyvinyl esters, polyvinylbutyrate, polyvinylformal, polyamides, polymethylmethacrylate, polybutylmethacrylate, plasticized polyvinyl chloride, plasticized nylon, plasticized soft nylon, plasticized polyethylene terephthalate, natural rubber, polyisoprene, polyisobutylene, polybutadiene, polyethylene, polytetrafluoroethylene, polyvinylidene chloride, polyacrylonitrile, cross-linked polyvinylpyrrolidone, polytrifluorochloroethylene, chlorinated polyethylene, poly(1,4'-isopropylidene diphenylene carbonate), vinylidene chloride, acrylonitrile copolymer, vinyl chloride-diethyl fumarate copolymer, butadiene/styrene copolymers, silicone rubbers, especially the medical grade polydimethylsiloxanes, ethylene-propylene rubber, silicone-carbonate copolymers, vinylidene chloride-vinyl chloride copolymer, vinyl chloride-acrylonitrile copolymer and vinylidene chloride-acrylonitride copolymer.

The illustrated embodiment includes a tab 10 which may be made of a wide variety of materials, including those mentioned above for the matrix material and/or the holder. Tab 10 may be provided in order to attach the device to a desired location in the eye, for example, by suturing. For the illustrated embodiment, tab 10 is made of PVA and is adhered to the inner drug core 2 with adhesive 11. Adhesive 11 may be a curable silicone adhesive, a curable PVA solution, or the like. If it is not necessary to suture the device in the eye, element 10 may have a smaller size such that it does not extend substantially beyond holder 6.

According to preferred embodiments, the holder is extracted to remove residual materials therefrom. For example, in the case of silicone, the holder may include lower molecular weight materials such as unreacted monomeric material and oligomers. It is believed that the presence of such residual materials may also deleteriously affect adherence of the holder surfaces. The holder may be extracted by placing the holder in an extraction solvent, optionally with agitation. Representative solvents are polar solvents such as isopropanol, heptane, hexane, toluene, tetrahydrofuran (THF), chloroform, supercritical carbon dioxide, and the like, including mixtures thereof. After extraction, the solvent is preferably removed from the holder, such as by evaporation in a nitrogen box, a laminar flow hood or a vacuum oven.

If desired, the holder may be plasma treated, following extraction, in order to increase the wettability of the holder and improve adherence of the drug core and/or the tab to the holder. Such plasma treatment employs an oxidation plasma in an atmosphere composed of an oxidizing media such as oxygen or nitrogen containing compounds: ammonia, an aminoalkane, air, water, peroxide, oxygen gas, methanol, acetone, alkylamines, and the like, or appropriate mixtures thereof including inert gases such as argon. Examples of mixed media include oxygen/argon or hydrogen/methanol. Typically, the plasma treatment is conducted in a closed chamber at an electric discharge frequency of 13.56 Mhz, preferably between about 20 to 500 watts at a pressure of about 0.1 to 1.0 torr, preferably for about 10 seconds to about 10 minutes or more, more preferably about 1 to 10 minutes.

The device may be sterilized and packaged. For example, the device may be sterilized by irradiation with gamma radiation.

It will be appreciated the dimensions of the device can vary with the size of the device, the size of the inner drug core, and the holder that surrounds the core or reservoir. The physical size of the device should be selected so that it does not interfere with physiological functions at the implantation site of the mammalian organism. The targeted disease state, type of mammalian organism, location of administration, and agents or agent administered are among the factors which would effect the desired size of the sustained release drug delivery device. However, because the device is intended for placement in the eye, the device is relatively small in size. Generally, it is preferred that the device, excluding the suture tab, has a maximum height, width and length each no greater than 10 mm, more preferably no greater than 5 mm, and most preferably no greater than 3 mm.

The examples and illustrated embodiments demonstrate some of the sustained release drug delivery device designs for the present invention. However, it is to be understood that these examples are for illustrative purposes only and do not purport to be wholly definitive as to the conditions and scope. While the invention has been described in connection with various preferred embodiments, numerous variations will be apparent to a person of ordinary skill in the art given the present description, without departing from the spirit of the invention and the scope of the appended claims.

What is claimed:

1. A method for making a drug delivery device, comprising:
    providing a holder made of a material impermeable to passage of an active agent, said holder being shaped to receive a drug core that includes the active agent;
    adding a curable liquid to the holder, and inserting a pin in the holder to displace the curable liquid;
    curing the liquid and removing the pin; and
    inserting the drug core into the holder.

2. The method of claim 1, wherein the drug core is shaped similarly as the pin.

3. The method of claim 1, wherein the holder includes at least one opening for passage of the pharmaceutically agent.

4. The method of claim 1, further comprising, after insertion of the drug core, covering the drug core with a layer of material.

5. The method of claim 4, wherein the layer of material includes a suture tab.

6. The method of claim 1, wherein the impermeable material comprises silicone.

7. The device of claim 1, wherein the drug core comprises a mixture of the active agent and a matrix material permeable to said active agent.

8. The method of claim 7, wherein the matrix material comprises polyvinyl alcohol.

9. The method of claim 1, wherein the curable liquid comprises polyvinyl alcohol.

10. The method of claim 1, wherein the liquid is cured by heating the device.

11. The method of claim 1, wherein the holder comprises a cylinder that surrounds the inserted drug core.

12. The method of claim 11, wherein an end of the cylinder includes at least one opening.

13. The method of claim 1, wherein the drug core is cylindrical.

14. The method of claim 1, wherein the drug core is coated with a material permeable to said active agent.

15. The method of claim 1, further comprising inserting a preformed disc of material in the holder, followed by adding the curable liquid to holder and preformed disc.

16. The method of claim 15, wherein the holder is cylindrical and the disc is circular.

17. The method of claim 16, wherein an end of the cylinder includes at least one opening, and the disc covers the at least one opening.

18. The method of claim 15, wherein the disc is made of a material permeable to the active agent.

19. The method of claim 15, wherein the disc is made of polyvinyl alcohol.

20. The method of claim 15, further comprising, after insertion of the drug core, covering the drug core with a layer of material including a suture tab.

* * * * *